United States Patent
Zhang

(10) Patent No.: US 9,949,653 B2
(45) Date of Patent: Apr. 24, 2018

(54) PATIENT SIGNAL ANALYSIS BASED ON VECTOR ANALYSIS

(71) Applicant: Siemens Medical Solutions USA, Inc., Malvern, PA (US)

(72) Inventor: Hongxuan Zhang, Austin, TX (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/621,917

(22) Filed: Jun. 13, 2017

(65) Prior Publication Data

US 2017/0273586 A1    Sep. 28, 2017

Related U.S. Application Data

(63) Continuation of application No. 14/541,619, filed on Nov. 14, 2014, now Pat. No. 9,782,092.

(51) Int. Cl.
| | |
|---|---|
| *A61B 5/00* | (2006.01) |
| *A61B 5/04* | (2006.01) |
| *A61B 5/0464* | (2006.01) |
| *A61B 5/0456* | (2006.01) |
| *A61B 5/046* | (2006.01) |
| *A61N 1/365* | (2006.01) |

(52) U.S. Cl.
CPC ...... *A61B 5/04011* (2013.01); *A61B 5/04012* (2013.01); *A61B 5/7235* (2013.01); *A61B 5/046* (2013.01); *A61B 5/0456* (2013.01); *A61B 5/0464* (2013.01); *A61N 1/36514* (2013.01)

(58) Field of Classification Search
CPC ........................ A61B 5/04011; A61B 5/04012
USPC .................................................. 600/517, 512
See application file for complete search history.

(56) References Cited

U.S. PATENT DOCUMENTS

| | | |
|---|---|---|
| 5,135,004 A | 8/1992 | Adams |
| 5,199,428 A | 4/1993 | Obel |
| 5,203,326 A | 4/1993 | Collins |
| 5,313,953 A | 5/1994 | Kreyenhagen |
| 5,330,507 A | 7/1994 | Schwartz |
| 5,497,780 A | 3/1996 | Zehender |
| 5,531,768 A | 7/1996 | Alferness |
| 6,128,526 A * | 10/2000 | Stadler ............ A61B 5/0452 600/517 |

* cited by examiner

*Primary Examiner* — Nadia A Mahmood

(57) ABSTRACT

Disclosed herein is a framework for facilitating patient signal analysis based on vector analysis. In accordance with one aspect, a set of vectors is generated from a patient signal data waveform. The vectors may be directed from a common center to points of interest on the patient signal data waveform. The framework may further extract one or more vector parameters from the set of vectors, and determine one or more vector ratios based on the vector parameters to monitor changes in the patient signal data waveform.

21 Claims, 8 Drawing Sheets

PATIENT SIGNAL ANALYSIS BASED ON VECTOR ANALYSIS

CROSS-REFERENCE TO RELATED APPLICATION

This patent application is a continuation and claims the benefit of priority under 35 USC § 120 to pending U.S. application Ser. No. 14/541,619, filed on Nov. 14, 2014.

TECHNICAL FIELD

The present disclosure generally relates to systems and methods for analyzing and characterizing patient signals

BACKGROUND

Coronary artery disease (CAD) is one of the most common causes of death in the United States, accounting for nearly 500,000 deaths each year. Studies estimate that 50% of men and 33% of women under the age of 40 will develop some form of CAD sometime during their lifetime. Sudden cardiac death has steadily accounted for approximately 50% of all heart-related, out-of-hospital deaths and improved clinical procedures almost entirely ignore this group. The fact that patients generally fail to recognize their symptoms and seek prompt medical attention contributes to these tragic statistics. The principal manifestations of CAD are coronary artherosclerosis (hardening of coronary arteries) or stenosis (narrowing of arteries), both of which ultimately force a reduction of the coronary circulation (myocardial ischemia, infarction, or other kind of cardiac arrhythmia). However, the early stages of CAD are usually non-symptomatic and invisible with current clinical cardiac signal analysis strategies.

Early arrhythmia recognition is critical for rhythm management of cardiac disorders. Currently, signal waveform and time domain parameter analysis of cardiac cycle depolarization and repolarization, such as P wave, QRS complex, ST segment, T wave, are used for cardiac arrhythmia monitoring and identification. However, such traditional clinical methodologies are sometimes subjective and time-consuming, requiring the user to possess expertise and clinical experience to achieve accurate interpretation and proper cardiac rhythm management.

Traditional medical methods usually focus on time domain analysis (e.g., amplitude, latency, etc.) or frequency domain analysis (e.g., power, spectrum, etc.), which may not accurately capture minute signal changes in the partial signal portion (e.g., P wave, QRS complex, ST segment, etc.) of cardiac activities. Such signal changes are usually invisible in signal wave morphology display or require extensive clinical expertise to achieve accurate diagnosis. Consequently, it may result in high failure rate of arrhythmia diagnosis and high number of false alarms. For example, a false negative (FN) results when the screening test wrongly makes the decision that a subject does not have disease X (e.g., myocardial ischemia) when he or she does in fact have the disease. These concerns raise a need for a new approach to precisely extract arrhythmia pathology information with high reliability and sensitivity from ongoing cardiac signals, which can diagnose partial signal portions of heart tissues.

Further, traditional methods based on voltage amplitude changes and variation analysis may not be sufficient for cardiac function evaluation and pathology diagnosis, especially since there is no quantitative link between the myocardial ischemia event/status and the amplitude and variation index. Known clinical diagnosis of myocardial ischemia (MI) and detection of infarction are based on the gold clinical standard based on ST segment voltage deviation (e.g., 0.1 mV elevation for myocardial ischemia detection). However, there are at least two shortcomings with this gold standard: (a) this standard only works for surface ECG signals, but not for intra-cardiac electrogram (ICEG) signals; (b) ST segment deviation (voltage) cannot be utilized as a quantitative method for myocardial ischemia severity diagnosis and characterization.

Current methods may not be able to qualitatively and quantitatively capture or characterize minute signal changes and predict the pathological trend, especially in the early stage of tissue malfunctioning and acute myocardial ischemia. Known methods may not efficiently analyze and predict the real-time growing trend of cardiac arrhythmias, such as the pathology trend from low risk to medium risk, and then to high risk (i.e., severe and fatal) rhythm, especially for life threatening arrhythmia, such as ventricular tachycardia (VT).

SUMMARY

The present disclosure relates to a framework for facilitating patient signal analysis based on vector analysis. In accordance with one aspect, a set of vectors is generated from a patient signal data waveform. The vectors may be directed from a common center to points of interest on the patient signal data waveform. The framework may further extract one or more vector parameters from the set of vectors, and determine one or more vector ratios based on the vector parameters to monitor changes in the patient signal data waveform.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
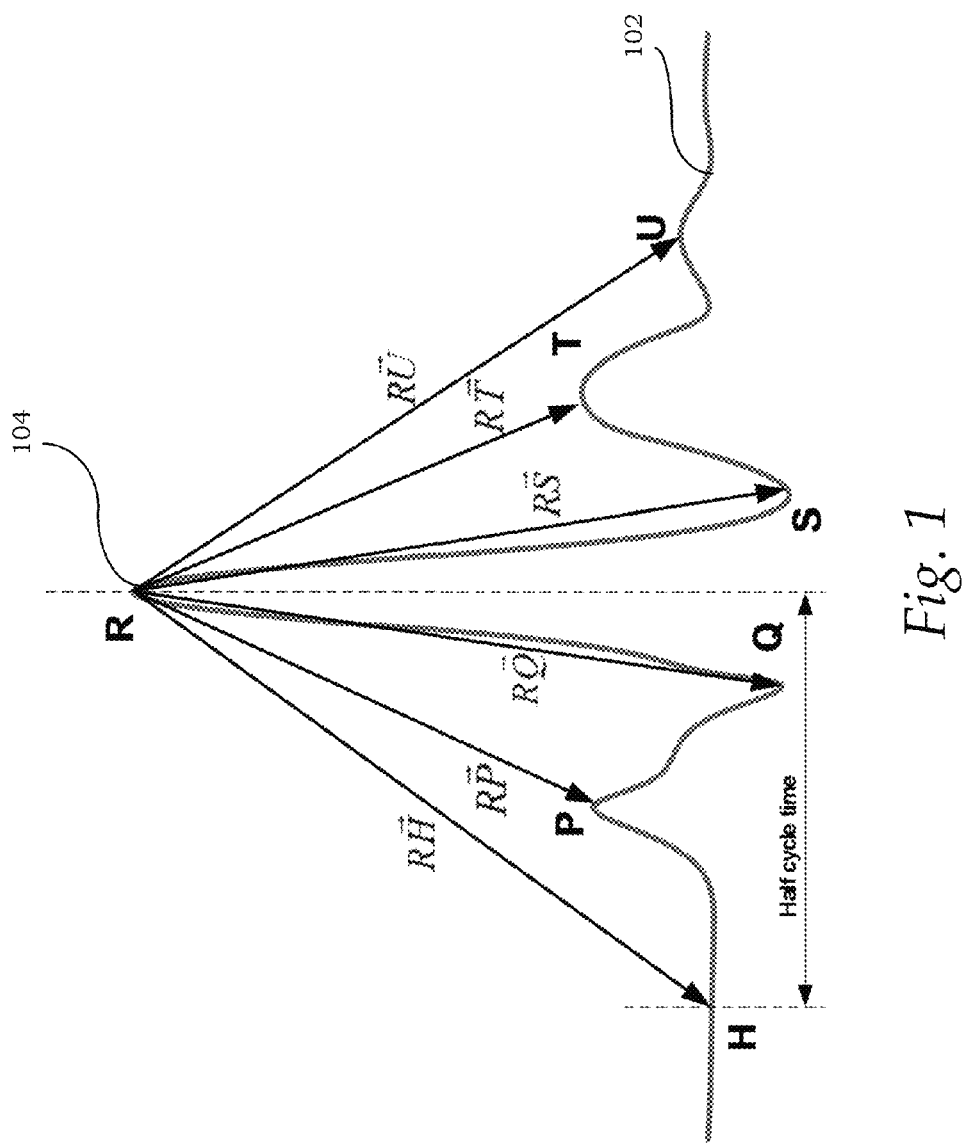
FIG. 1 illustrates an exemplary signal vector system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present framework provides a methodology to analyze patient signals. In accordance with one aspect, the present framework analyzes electrophysiological function signals (e.g., surface ECG signals, ICEG signals, etc.) based on region of interest (ROI) signal portion shape and morphology changes. Such analysis may use dynamic signal vector parameter values, vector ratios and statistical distribution of the ROI signal waveform morphologies to characterize minute signal data variation. By providing qualitative and quantitative evaluation of change ratios of different portions of the signal waveform, including the use of unilateral and/or bilateral ROI signal vector ratios of different signal portions, the accurate time stamp, location, type and severity of cardiac myocardial pathology and clinical events may be more precisely and reliably diagnosed, detected, mapped and characterized. The present framework advantageously provides a more efficient, accurate and reliable method for identifying cardiac function disorders, differentiating cardiac arrhythmias, characterizing heart pathological severities and tissue location, predicting life-threatening events, and/or evaluating the drug delivery and effects.

FIG. 1 illustrates an exemplary ROI signal vector system. The ROI signal vector system is generated based on a waveform 102. Waveform 102 is a typical waveform that may be generated from an electrophysiological signal (e.g., surface or intra-cardiac ECG). The waveform 102 reflects the electrical activity of the heart, with time represented on the horizontal axis (or x axis) and voltage represented on the vertical axis (or y axis). The waveform 102 may be categorized or segmented by several different ways, such as signal peak timing, signal amplitude range, etc. In accordance with some implementations, the whole cycle of the electrophysiological signal is divided by ROI signal vectors, distance circles of vectors and/or vector time durations.

In some implementations, the signal vector system is centered at a common R wave peak point 104 of the waveform 102. Different vectors (e.g., $R\vec{H}, R\vec{P}, R\vec{Q}, R\vec{S}, R\vec{T}$ and $R\vec{U}$) originating from the R wave peak 104 to points of interest on the waveform 102 may be defined. Points of interest may include P, Q, S, T, U wave peak points and an H point of the waveform 102. The H point may be defined at a half cardiac cycle time point of the waveform 102 measured from the R peak time, and can be used to determine the resting stage vector $R\vec{H}$. Clinically, these vectors represent the energy and amplitude differences and flows, which can be used to calculate waveform distribution changes due to cardiac arrhythmia or pathology events. It should be appreciated that the signal vector system may also be centered at a common point other than the R wave peak 104, and similar vectors originating from such common center to other points of interest may also be defined. For example, software or clinical users may define similar signal vectors and associated ratios based on the application and clinical needs, such as T wave centered vectors: $T\vec{H}, T\vec{P}$, and etc. Other peaks of the waveform 102 may also be used as a center point for vector creation.

Figure 2:
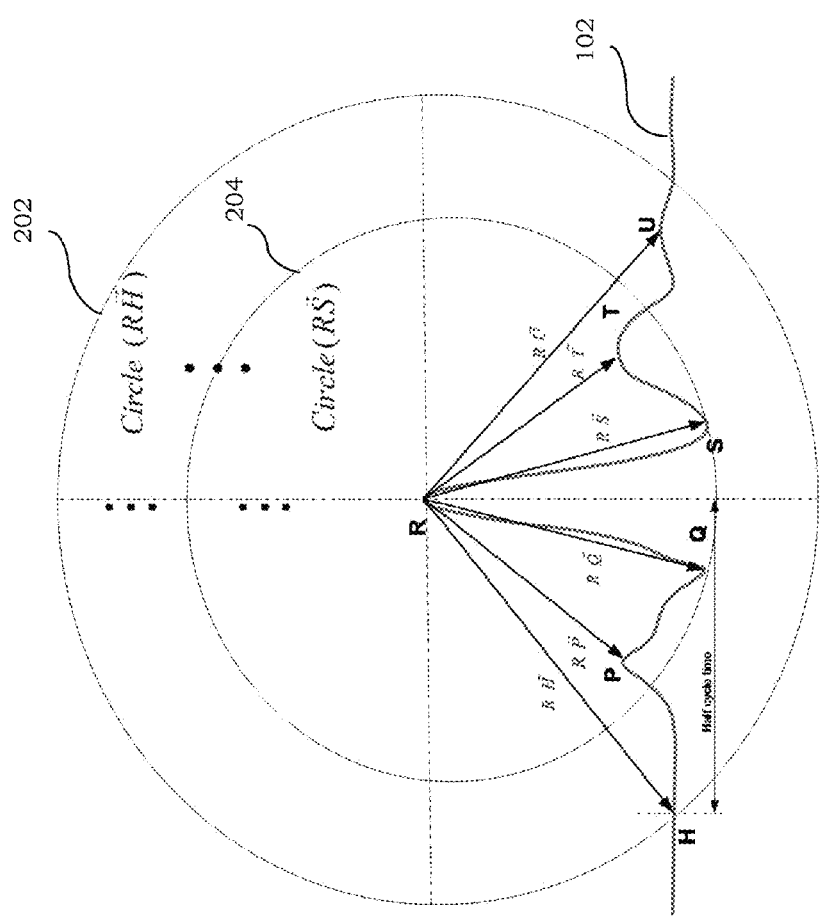
FIG. 2 illustrates an exemplary vector circle-based segmentation.

By using such vector definition and segmentation, the whole cardiac cycle may be further categorized by vector circles. In accordance with some implementations, a mapping based on vector circles is provided to generate a two-dimensional visualization of the signal amplitude range, energy size, cardiac vector scanning area, etc. FIG. 2 illustrates an exemplary vector circle-based segmentation. For purposes of illustration, two vector circles centered at an R wave peak are shown: Circle($R\vec{H}$) 202 and Circle($R\vec{S}$)) 204. However, it should be appreciated that other number and/or types of vector circles may also be defined based on other points of interest. Different vectors and vector circles may be utilized to qualitatively illustrate and quantitatively calculate minute signal changes and distortion due to cardiac arrhythmia and medical events.

Each vector circle may be centered at the R wave peak (or other vector center points) with a radius defined by one of the vectors. In this example, the radius of the vector circle Circle($R\vec{H}$) 202 is defined by the $R\vec{H}$ vector, while the radius of the vector circle Circle($R\vec{S}$) is defined by the $R\vec{S}$ vector. It can be determined in this example that Circle($R\vec{H}$) 202 is the biggest circle and covers the entire cardiac cycle. Other vector circles centered at the R wave peak may also be defined based on other vectors (e.g., $R\vec{P}, R\vec{Q}, R\vec{T}$ or $R\vec{U}$). Accordingly, one-dimensional vectors may be mapped to their respective two-dimensional circles. The shapes, areas or sizes of the vector circles may then be compared to calculate the quantitative energy-amplitude and timing difference for characterizing cardiac functionality.

Figure 3:
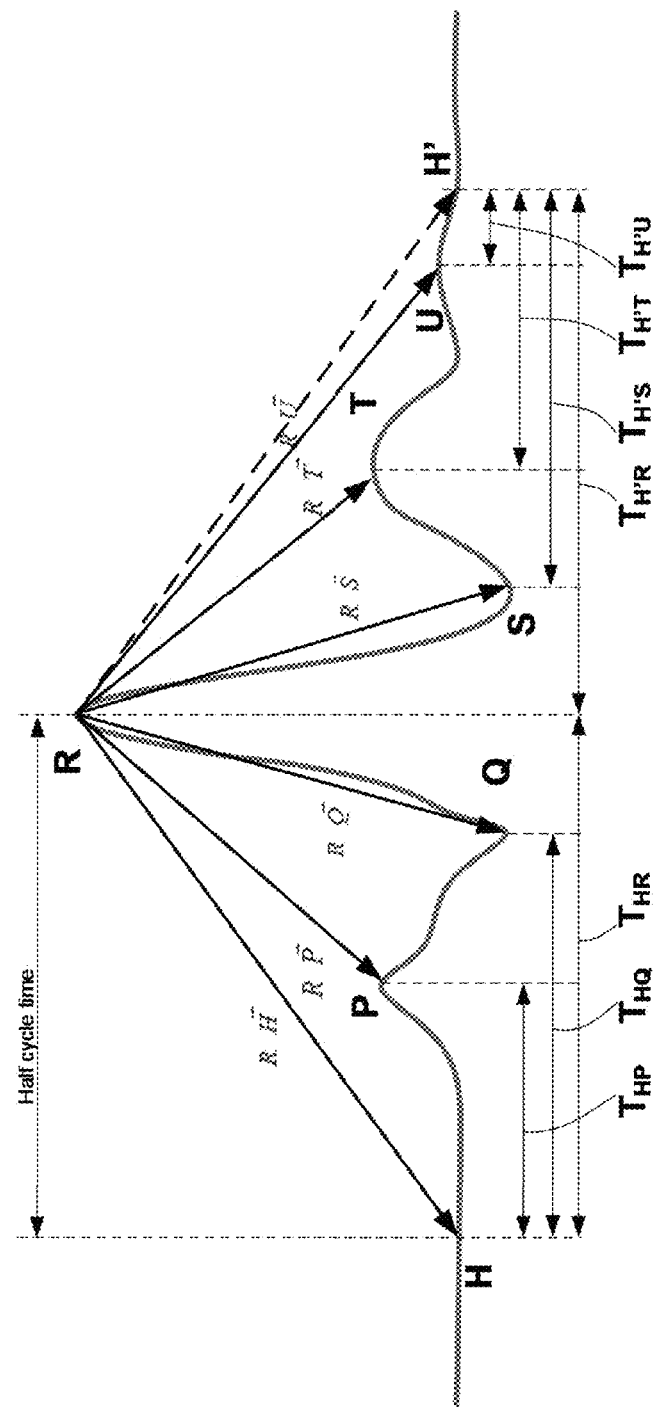
FIG. 3 shows exemplary vector time durations.

Vector time durations may further be defined to more efficiently analyze cardiac waveform changes. FIG. 3 shows exemplary vector time durations. These vector time durations may be integrated into cardiac waveform vector analysis and used for monitoring cardiac ROI timing. As shown, the time durations (e.g., $T_{HP}$, $T_{HQ}$, $T_{HR}$, $T_{H'R}$, $T_{H'S}$, $T_{H'T}$, $T_{H'U}$, etc.) are measured from H or H' to the time stamps of the points of interest (e.g., P, Q, R, S, T, U peak points). H or H' are two half cycle time stamps from the R wave peak timing. H and H' may be derived by using RR wave detection. Accordingly, by using the time calibration of H and H' points, different vector time durations may be defined. These timing parameters correspond to the R wave signal vectors (e.g., $\vec{RH}$, $\vec{RP}$, $\vec{RQ}$, $\vec{RS}$, $\vec{RT}$ and $\vec{RU}$) and can be used for cardiac functionality characterization.

Figure 4:
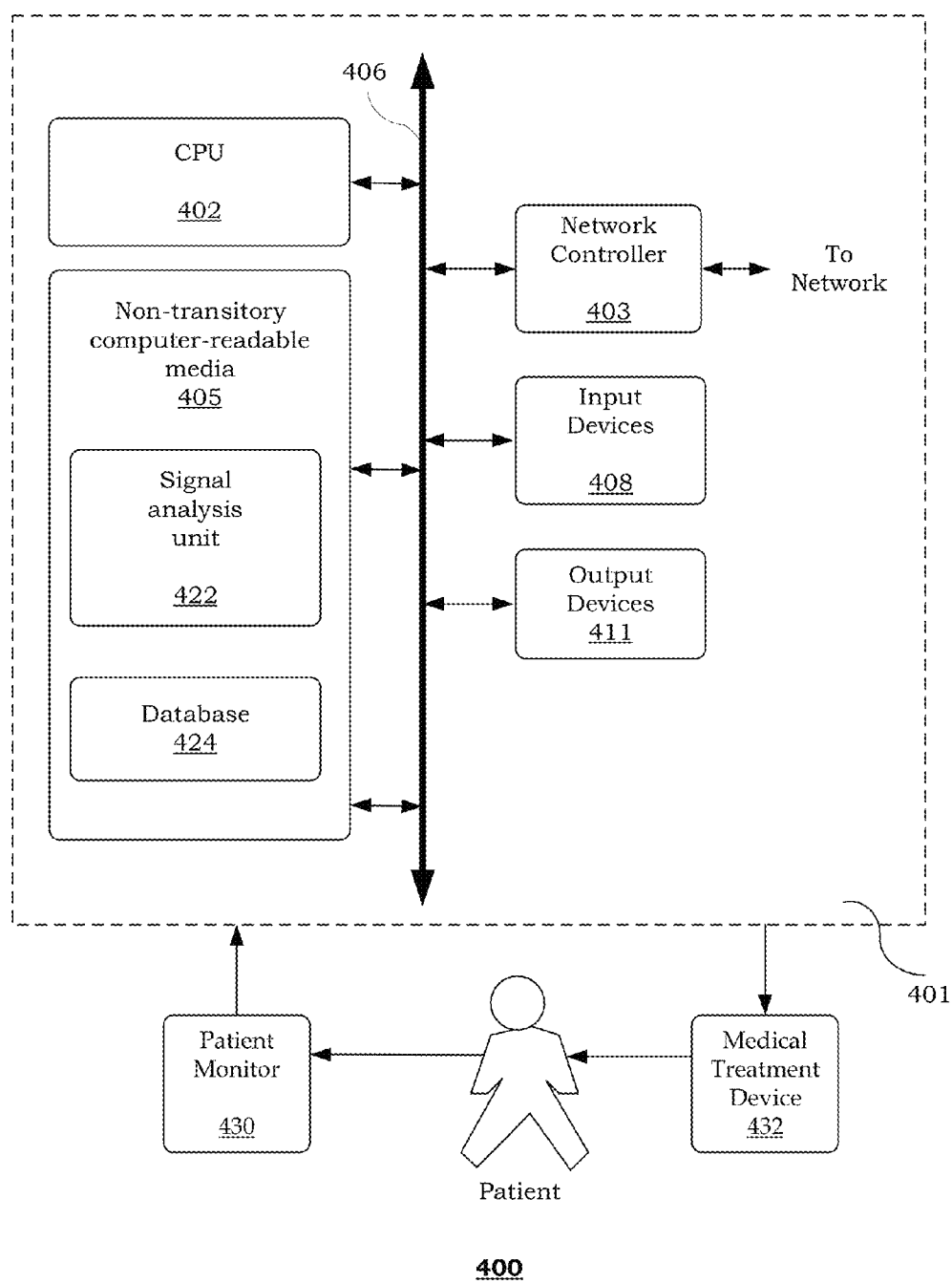
FIG. 4 shows an exemplary system.

FIG. 4 shows an exemplary system 400 for implementing a method and system of the present disclosure. It is to be understood that, because some of the constituent system components and method steps depicted in the accompanying figures can be implemented in software, the actual connections between the systems components (or the process steps) may differ depending upon the manner in which the present framework is programmed. For example, the system 400 may be implemented in a client-server, peer-to-peer (P2P) or master/slave configuration. In such configurations, the system 400 may be communicatively coupled to other systems or components via a network, such as an Intranet, a local area network (LAN), a wide area network (WAN), a P2P network, a global computer network (e.g., Internet), a wireless communications network, or any combination thereof. Given the teachings of the present invention provided herein, one of ordinary skill in the related art will be able to contemplate these and similar implementations or configurations of the present invention.

As shown in FIG. 4, the system 400 may include a computer system 401, a patient monitor 430 and a medical treatment device 432. In some implementations, the computer system 401 is implemented as an implantable cardiac pacing control device (ICD), as will be discussed in more detail later. Other implementations, such as a server, desktop computer, mobile computing device, laptop, tablet, etc., are also possible. The computer system 401 may include, inter alia, a central processing unit (CPU) 402, a non-transitory computer-readable media 405, one or more output devices 411 (e.g., printer, display monitor, projector, speaker, etc.), a network controller 403, an internal bus 406 and one or more input devices 408, for example, a keyboard, mouse, touch screen, gesture and/or voice recognition module, etc. Computer system 401 may further include support circuits such as a cache, a power supply, clock circuits and a communications bus. Various other peripheral devices, such as additional data storage devices and printing devices, may also be connected to the computer system 401.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 405. Non-transitory computer-readable media 405 may include random access memory (RAM), read only memory (ROM), magnetic floppy disk, flash memory, and other types of memories, or a combination thereof. The present techniques may be implemented by patient signal analysis unit 422 that is stored in computer-readable media 405. As such, the computer system 401 is a general-purpose computer system that becomes a specific-purpose computer system when executing the computer-readable program code.

The same or different computer-readable media 405 may be used for storing a database 424. Database 424 may include a repository of determined parameters, indices and/or ratios, selectable predetermined functions, patient signal data (e.g., electrophysiological, ECG, ICEG, respiration signal data, other hemodynamic or vital sign data, etc.), patient data (e.g., demographic data, pathology history, etc.), other input data and/or other derived output parameters. Patient signal data may be provided by a patient monitor 430 that is communicatively coupled to the computer system 401.

Patient monitor 430 may be used to acquire various types of patient biometric or electrophysiological signal information for monitoring the patient. For example, the monitoring information may include, but is not limited to, electrophysiological signal data (e.g., ECG, ICEG, etc.), oximetric or SPO2 signal data, respiration signal data, blood pressure, temperature and/or other patient biometric, physiological, hemodynamic, vital sign or medical parameter information. The patient monitor 430 may include appropriate biometric sensors (e.g., leads for surface ECG and basket catheter for intra-cardiac electrographic signal data) for acquiring the monitoring patient signals. Implementations of the present framework provide parameters and/or indices to detect, diagnose and quantify such patient signals.

Medical treatment device 432 may be automatically and adaptively controlled by the computer system 401 in a closed-loop feedback control system. Medical treatment device 432 may include, but are not limited to, a pacing device, ablator, cardioverter, defibrillator, and so forth. Control parameters of the medical treatment device 432, such as the pacing parameter, ablation energy control, etc., may be automatically determined by computer system 401.

Figure 5:
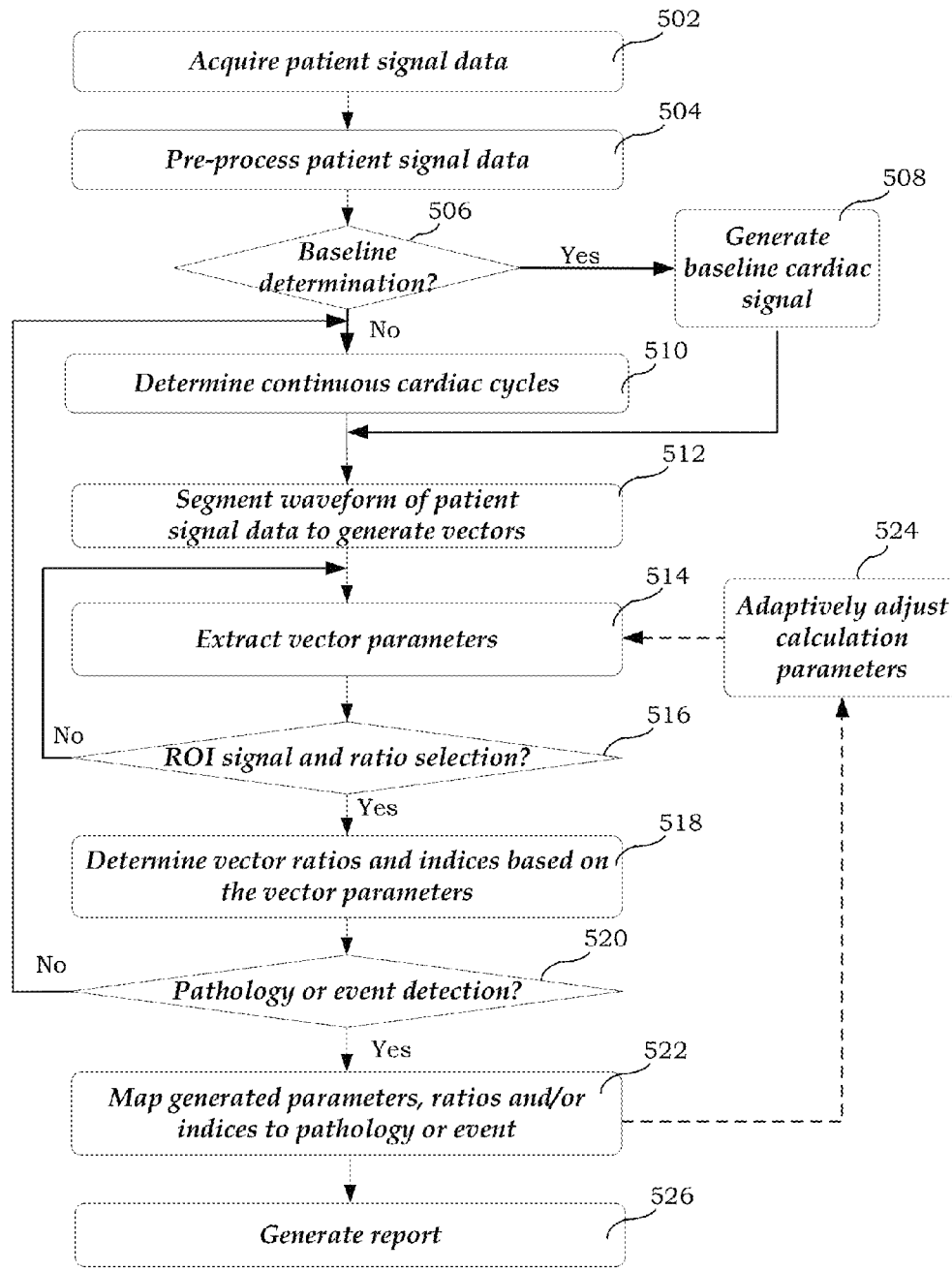
FIG. 5 shows an exemplary method of analyzing patient signals based on vector analysis.

FIG. 5 shows an exemplary method 500 of analyzing patient signals based on vector analysis. The steps of the method 500 may be performed in the order shown or a different order. Additional, different, or fewer steps may be provided. Further, the method 500 may be implemented with the system 400 of FIG. 4, a different system, or a combination thereof.

At 502, patient monitor 430 acquires patient signal data from a current patient. In some implementations, the patient signal data comprises cardiac electrophysiological signal data, such as intra-cardiac electrographic (ICEG) data, surface ECG data, etc. The patient signal data may be represented by a waveform or graph, with time represented on the x-axis and voltage represented on the y-axis. The cardiac electrophysiological signal data may be acquired by multiple channels connected to an intra-cardiac basket catheter placed into, for example, the right atrium of the heart. Alternatively, or additionally, other types of electrophysiological signal data, such as hemodynamic (HEMO) signal data (e.g., invasive blood pressure, non-invasive blood pressure signal data, cardiac output signals, etc.), respiration (or capnographic) signal data, blood pressure data, oximetric (SPO2) data, and/or other vital sign signal data, other measurable patient biometric, physiological or medical signals, may also be acquired. In addition, other patient information, such as demographic data, clinical application and patient status, including, but not limited to, weight, height, gender, age, allergies, medications, pathology history, pathology treatment history, etc., may also be acquired.

At 504, the patient signal data is pre-processed. The patient signal data may be pre-processed by conditioning, filtering, amplification, digitization and/or buffering. For example, the patient signal data may be pre-filtered and amplified for display on, for instance, patient monitor 430. The patient signal data may be filtered to remove unwanted patient movement and respiratory artifacts, as well as power line noise. The filter may be adaptively selected in response to data indicating clinical application (e.g. ischemia detection application, rhythm analysis application). The patient signal data may be conditioned, amplified, buffered, filtered and/or digitized to produce a continuous stream of digitized samples.

At 506, patient signal analysis unit 422 may determine whether a baseline value or signal is to be automatically extracted from the digitized patient signal data. The baseline value (or signal) generally refers to a known threshold value (or benign signal) with which an unknown value (e.g., amplitude) is compared when measured or assessed. The baseline value may be used in, for example, threshold determination, computation of parameters or indices, and so forth.

If the baseline value or signal is to be automatically determined, at 508, patient signal analysis unit 422 automatically generates the baseline cardiac value or signal. The baseline value may comprise a zero voltage line if a static (DC) voltage signal component is filtered out from the signal. The baseline value may be adaptively adjusted according to the current application and clinical requirements. Alternatively, if the value is not to be automatically determined, the user may manually select it via, for example, a user interface.

At 510, patient signal analysis unit 422 determines continuous cardiac cycles. Continuous cardiac cycles may be determined by, for example, R wave detection using an amplitude threshold for R waves.

At 512, patient signal analysis unit 422 performs segmentation of the waveform of the patient signal data. The segmentation may be performed within a region of interest in the waveform. The region of interest (ROI) may be any portion of the waveform that is identified for further analysis.

The segmentation is performed to generate vectors that are directed from a common center (or origin) to points of interest on the waveform of the patient signal data, as previously described with reference to FIG. 1. The segmentation is performed by first detecting a vector center in the continuous cardiac cycles. The vector center serves as the point from which the vectors originate. In some implementations, the vector center is the R wave peak point. The R wave is also known as the intrinsicoid deflection, which represents the time taken for excitation to spread from the endocardial to the epicardial surface of the left ventricle of the heart. Other points of interest on the waveform, such as the H, P, Q, S, T and U key points, may also be detected. Such points of interest may be determined by, for example, a peak detector. After the center and points of interest are detected, vectors (e.g., $\vec{RH}$, $\vec{RP}$, $\vec{RQ}$, $\vec{RS}$, $\vec{RT}$ and $\vec{RU}$) may be defined from the center to the points of interest.

At 514, patient signal analysis unit 422 extracts one or more vector parameters from the generated vectors. The one or more vector parameters may include any parameters that may be defined and measured based on the vector segmented waveform. Types of vector parameters include, but are not limited to, vector circles centered at a common center and radius defined by one of the generated vectors (such as those previously described with respect to FIG. 2) or vector time durations measured from a half cycle time stamp to time stamps of the points of interest (such as those previously described with respect to FIG. 3).

At 516, patient signal analysis unit 422 determines if ROI signal and ratio selection is to be performed. Depending on the clinical application and/or user experience, ROI signal and ratio selection may be performed. If ROI signal and ratio selection is not to be performed, the method 500 returns to step 514. If yes, the method 500 proceeds to the next step 518.

At 518, patient signal analysis unit 422 determines one or more vector ratios and indices based on the vector parameters to monitor changes in the patient signal data waveform. Vector ratios may include, but are not limited to, distance ratios, time duration ratios, amplitude to time duration ratios (or time duration to amplitude ratios), energy area ratios, energy area to time duration ratios, etc. Vector indices may include, but are not limited to, unilateral and bilateral vector ratio indices, as well as statistical indices.

In some implementations, a distance ratio that compares distances of different vectors is determined as follows:

$$\text{Vector\_Ratio}_{ROI1-ROI2} = \left|\frac{\text{ROI1\_Vector}}{\text{ROI2\_Vector}}\right| \quad (1)$$

wherein $\text{Vector\_Ratio}_{ROI1-ROI2}$ is the ratio of distances associated with two different corresponding vectors ROI1_Vector and ROI2_Vector originating from a common center on the waveform. In some implementations, ROI1_Vector and ROI2_Vector are any two different vectors originating from the R wave peak to different points of interest (e.g., $\vec{RH}$, $\vec{RP}$, $\vec{RQ}$, $\vec{RS}$, $\vec{RT}$ or $\vec{RU}$) on the waveform. The $\text{Vector\_Ratio}_{ROI1-ROI2}$ may be used to monitor vector distance distortion. For example, the ratio of $\vec{RP}$ to $\vec{RU}$ distances shows the vector distance difference between the P wave and U wave, and is indicative of combination changes of the ROI signal timings and voltage amplitudes, relative to the R wave.

In some implementations, a time duration ratio that compares time durations of different vectors may be determined as follows:

$$\text{Vector\_timing\_Ratio}_{ROI1-ROI2} = \left|\frac{\text{ROI1\_Vector\_timing}}{\text{ROI2\_Vector\_timing}}\right| \quad (2)$$

wherein $\text{Vector\_ti min g\_Ratio}_{ROI1-ROI2}$ is the ratio of time durations associated with two different vectors originating from the same center (e.g., R wave peak). Such time durations may be selected from the set of time durations: $T_{HP}$, $T_{HQ}$, $T_{HR}$, $T_{H'R}$, $T_{H'S}$, $T_{H'T}$, and $T_{H'U}$, as previously described with reference to FIG. 3. The $\text{Vector\_ti min g\_Ratio}_{ROI1-ROI2}$ shows the difference or latency change between the respective vector time durations. For example, the time duration ratio of $T_{HP}$ to $T_{HQ}$ is indicative of the combination change of the ROI signal timing and latency, particularly the dynamic changes in the P wave portion or the atrial electrophysiological activity.

In some implementations, a vector amplitude to time duration ratio Vector_Amp_Time_Ratio$_{ROI1-ROI2}$ is determined as follows:

$$\text{Vector\_Amp\_Time\_Ratio}_{ROI1-ROI2} = \left| \frac{\text{ROI1\_Vector\_Amp}}{\text{ROI2\_Vector\_Time}} \right| \quad (3)$$

Alternatively, or additionally, a vector time duration to amplitude ratio Vector_Time_Amp_Ratio$_{ROI1-ROI2}$ may be determined as follows:

$$\text{Vector\_Time\_Amp\_Ratio}_{ROI1-ROI2} = \left| \frac{\text{ROI1\_Vector\_Time}}{\text{ROI2\_Vector\_Amp}} \right| \quad (4)$$

wherein ROIi_Vector_Amp denotes the amplitude (i.e., distance or size) of vector ROI_vector$_i$ in the cardiac ROI signal portion and ROIi_Vector_Amp=|ROI_vector$_i$|, and i=1 or 2. The vector ROI vector, may be any one of these vectors: $\vec{RH}$, $\vec{RP}$, $\vec{RQ}$, $\vec{RS}$, $\vec{RT}$, and $\vec{RU}$. ROIi_Vector_Time denotes the ROI signal portion vector time duration, which may be any one of the timing durations: $T_{HP}$, $T_{HQ}$, $T_{HR}$, $T_{H'R}$, $T_{H'S}$, $T_{H'T}$, and $T_{H'U}$.

The cardiac signal amplitudes and time durations may be extracted from different ROI signal vectors, in which case the ratio is referred to as a "cross vector ratio." Alternatively, the cardiac signal amplitudes and time durations are extracted from the same ROI signal vector, in which case the ratio is referred to as a "uni-vector ratio." The cardiac ROI signal vector amplitude to time duration (or the vector time duration to amplitude ratio) is indicative of the change of speed of the signal waveform, which is also the energy charging or discharging speed for different stages of the myocardial electrophysiological dynamic activities. This ratio may be utilized for tracking cardiac functionality distortion, especially heart rate change in the signal amplitude.

In some implementations, a vector energy ratio is determined as follows:

$$\text{Vector\_Energy\_area\_Ratio}_{ROI1-ROI2} = \left| \frac{S(\text{ROI1\_map\_circle})}{S(\text{ROI2\_map\_circle})} \right| \quad (5)$$

wherein Vector_Energy_area_Ratio$_{ROI1-ROI2}$ is the ROI signal vector energy area ratio between vectors ROI1 and ROI2; S(•) is the function for calculating area, S(ROI1_map_circle) is the total area of the ROI1 vector circle and S(ROI2_map_circle) is the total area of the ROI2 vector circle. Exemplary vector circles were previously described with reference to FIG. 2. By using the ratio of the two vector circle areas, the energy difference and minute dynamic distortion due to cardiac pathologies and events may be characterized.

In some implementations, a vector energy area to time duration ratio is determined to compare the ROI signal vector energy with corresponding or other ROI signal vector time duration as follows:

$$\text{Vector\_Energy\_area\_to\_time\_Ratio}_{ROI1-ROI2} = \left| \frac{S(\text{ROI1\_map\_circle})}{\text{ROI2\_Vector\_timing}} \right| \quad (6)$$

wherein Vector_Energy_area_to_time_Ratio$_{ROI1-ROI2}$ is the ratio of ROI signal vector energy area associated with the vector circle of vector ROI1 to time duration associated with vector ROI2; S(•) is the function for calculating area; S(ROI1_map_circle) is the total area of the ROI1 vector circle; and ROI2_Vector_ti min g may be one of the time durations: $T_{HP}$, $T_{HQ}$, $T_{HR}$, $T_{H'R}$, $T_{H'S}$, $T_{H'T}$, and $T_{H'U}$. By using the vector circle area to corresponding vector time duration ratio, the instant (timing based) energy difference and minute dynamic distortion due to cardiac pathologies and events for specific cardiac electrophysiological stages can be captured and determined.

In the section above, different ratios and parameters are provided. These ratios and parameters may be used to track, detect and characterize the ROI or whole cardiac signal waveform changes in a single heart cycle, such as comparing the RT vector to RP vector, etc. The different ratios between different ROI portions within the same cardiac heart cycle are referred to herein as mutual or cross comparison vector signal ratios. ROI vectors from different cardiac cycles or episodes, such as healthy portion and signal portions of interest, may also be compared. In order to more efficiently illustrate minute signal changes in different portions, the different ratios may be integrated as unilateral or bilateral vector ratios. A unilateral vector ratio is based on the vector ratios of the same ROI vector portion and parameter within different heart cycles; while bilateral vector ratio index is based on the vector ratios of different ROI vector portions and parameters within different heart cycles.

Accordingly, exemplary unilateral ratios may be defined as follows:

$$\text{Vector\_Ratio}_{ROI1-ROI2}(i, j) = \left| \frac{\text{ROI1\_Vector}(i)}{\text{ROI2\_Vector}(j)} \right| \quad (7)$$

$$\text{Vector\_timing\_Ratio}_{ROI1-ROI2}(i, j) = \left| \frac{\text{ROI1\_Vector\_timing}(i)}{\text{ROI2\_Vector\_timing}(j)} \right| \quad (8)$$

$$\text{Vector\_Amp\_Time\_Ratio}_{ROI1-ROI2}(i, j) = \left| \frac{\text{ROI1\_Vector\_Amp}(i)}{\text{ROI2\_Vector\_Time}(j)} \right| \quad (9)$$

$$\text{Vector\_Energy\_area\_Ratio}_{ROI1-ROI2}(i, j) = \left| \frac{S(\text{ROI1\_map\_circle}, i)}{S(\text{ROI2\_map\_circle}, j)} \right| \quad (10)$$

$$\text{Vector\_Energy\_area\_to\_time\_Ratio}_{ROI1-ROI2}(i, j) = \quad (11)$$
$$\left| \frac{S(\text{ROI1\_map\_circle}, i)}{\text{ROI2\_Vector\_timing}(j)} \right|$$

wherein i and j denote first and second cardiac cycles, and ROI1 and ROI2 denote first and second ROI vector portions. If i=j, it means that cross or mutual vector signal ratios are being determined. If i is different from j but ROI1=ROI2, it means that unilateral cardiac vector signal ratios are being determined. If i is different from j and ROI1 is also different from ROI2, it means that bilateral cardiac vector signal ratios are being determined.

The aforementioned parameters and ratios are not only useful for single lead or channel cardiac electrophysiological signal, but also for cardiac signals from multiple leads or channels, which may include averaged or filtered signals or multi-heart-beat averaged cardiac cycle signals. For different channels or parameter-based signal vector ratio analysis, statistical analysis and information fusion may be used to obtain a more accurate, reliable and sensitive cardiac function diagnosis and pathology detection and characterization.

In some implementations, statistical indices are determined based on the generated ratios as follows:

Vector ratio Mean or Average value (expectation): $\text{mean}(X) = \frac{1}{W}\sum_{i \in W} X(i)$ (12)

Vector ratio Standard deviation: $STD(X) = \frac{1}{W-1}\sum_{i \in W-1}(X(i) - \text{mean}(X))$ (13)

Signal Vector Ratio Variation: $\text{Var}(X) = \frac{\text{mean}(X)}{STD(X)}$ (14)

Signal Vector Ratio Variability: $\text{Var\_b} = \frac{\max(X - \text{mean}(X))}{\text{mean}(X)}$ (15)

wherein X is the previously determined vector parameter or ratio (e.g., vector ratio, unilateral or bilateral ratios derived from vector parameters or ratios, etc.); and W is the calculation window size (i.e., there are W heartbeat cycles in a calculation window; heart cycle can be also derived from cardiac vector signals). In some implementations, the statistical indices may further include values derived by high order statistical calculation (HOS), tests methods (such as t-test) and/or hypothesis evaluations of the signals/data distributions.

At 520, patient signal analysis unit 422 determines if pathology or cardiac event detection is to be performed. If not, the method 500 returns to step 510. If yes, the method 500 proceeds to next step 522.

At 522, patient signal analysis unit 422 maps the generated vector parameters, ratios and/or indices to corresponding cardiac events or pathology (e.g., location, type, severity, trend, etc.). In most cases, the generated vector parameters, ratios and/or indices can provide good sensitivity and stability for diagnosing cardiac tissue and electrophysiological-hemodynamic malfunctions. However, the accuracy and reliability may be improved by combining all available patient data, such as other ECG signal data and derived parameters, non-invasive blood pressure (NIBP) or invasive blood pressure (IBP) signal data, etc.

Figure 6:
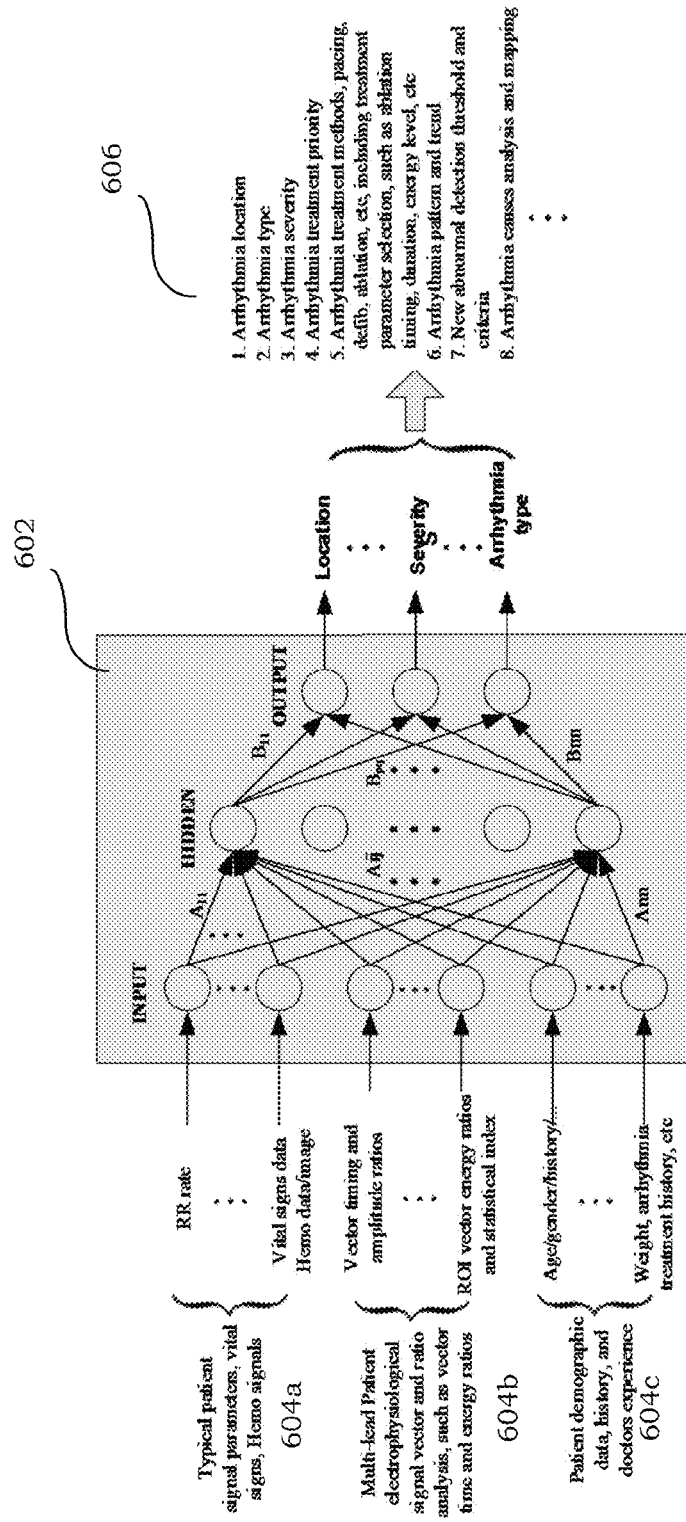
FIG. 6 shows an exemplary artificial neural network (ANN) module for multi-patient data fusion.

In some implementations, an artificial neural network (ANN) is used for nonlinear fusion of different types of patient data, including the vector parameters, ratios and/or indices generated by the present framework. FIG. 6 shows an exemplary ANN module 602 for multi-patient data fusion. There are 3 layers in the ANN module 602: input layer, hidden layer and output layer. $A_{ij}$ denote weights between the input layer and the hidden layer, while $B_{pq}$ denote weights between the hidden layer and the output layer. The weights $A_{ij}$ and $B_{pq}$ can be adaptively adjusted with training data set.

The ANN module 602 has self-learning capability with new input data 604, which can increase the accuracy of calculated results 606. The ANN module 602 combines typical signal parameters and vital sign data 604a, patient signal analysis results (e.g., vector parameters, energy ratios, statistical indices, etc.) 604b generated by the present framework, and patient data, history and doctor's knowledge 604c to generate output results 606 for detecting and treating emerging pathological events. More detailed patient status and treatment parameters 606 can be derived, via the ANN module 602, for achieving optimized cardiac rhythm management (CRM). Exemplary output parameters 606 include, but are not limited to, cardiac arrhythmia type, severity, location, time stamp, event trend, treatment parameter and suggestions (e.g., treatment location, priority, treatment control parameters, etc.). By using multi-channel signal data and multiple kinds of patient data, cardiac arrhythmia can be more efficiently detected and characterized. For instance, cardiac disorders and arrhythmias may be differentiated, pathological severities may be characterized, life-threatening events may be predicted, and drug delivery and effects may be evaluated.

At 524, patient signal analysis unit 422 may optionally adaptively adjust calculation parameters used for calculating the afore-mentioned vector parameters, ratios and/or indices. The adaptive adjustment may be performed automatically, semi-automatically or manually by the clinical user based on clinical experience and knowledge. Such calculation parameters may include, but are not limited to, calculation window size, signal portion, ROI area, time steps, severity thresholds, and so forth.

At 526, patient signal analysis unit 422 generates a patient report. The patient report may record the abnormality, associated characteristics (e.g., location, type, severity, timing, etc.) and other information (e.g., suggested treatment options). The patient report may be in the form of, for example, an alert message presented at patient monitor 430. The patient report may also be stored in database 424 for future retrieval, transmitted or shared with other client computers, and/or printed in physical form for viewing.

Figure 7:
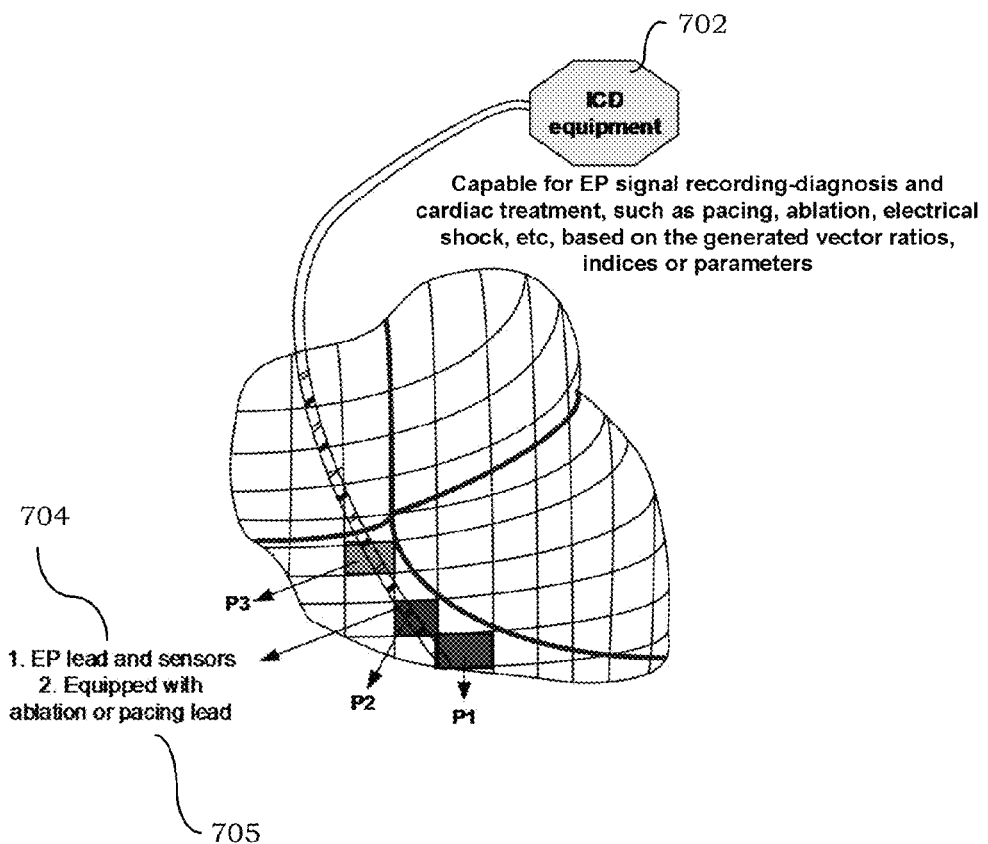
FIG. 7 illustrates a computer simulation of a multi-channel cardiac signal diagnostic application.

There may be many types of clinical applications that can employ the vector ratios, parameters and/or indices generated by the present framework. FIG. 7 illustrates a computer simulation of an exemplary multi-channel cardiac signal diagnostic application. The exemplary application may be implemented as, for example, an implantable cardiac pacing control device (ICD) 702. Based on the myocardial ischemia severity and level, appropriate medical treatment may be applied to efficiently save the life of the patient and reduce fatality risk from cardiac arrhythmia and pathologies.

The ICD equipment 702 may include, for example, the computer system 401 to implement the techniques described herein. The ICD equipment 702 may perform cardiac ROI signal vector analysis to generate vector parameters and associated ratios and/or indices, as well as traditional intra-cardiac signal analysis, such as ST segment voltage elevation. In some implementations, the ICD equipment 702 is coupled to an electrocardiogram recorder with multi-channel sensors and leads 704 to acquire an ongoing cardiac electrophysiological signal. As shown, three different leads (or positions P1, P2 and P3) may be provided to localize the cardiac arrhythmia mapping of the ventricular myocardial tissue.

The ICD equipment 702 may map the acquired signal data and generated vector parameters, ratios and/or indices to pathology characteristics (e.g., location, severity, treatment priorities, etc.) and treatment control parameters. The ICD device 702 may further be coupled to a cardiac ablation or pacing device 705 for treating or correcting heart rhythm problems. The cardiac ablation or pacing device 705 may be paired with the multi-channel sensors and leads 704, and controlled by the generated treatment control parameters to provide real-time treatment that is adaptive based on local signal data acquired from neighboring sites. For example, the ICD device 702 may adjust the size or duration of pacing energy, sequence of ablation, etc., according to the locally acquired signal data and associated treatment control parameters.

Figure 8:
FIG. 8 shows a table that includes calculation results based on the computer simulation.

In order to differentiate myocardial ischemia events, three different levels of myocardial ischemia severity were determined: (1) normal cardiac rhythm, (2) early ischemia and (3) early infarction (late ischemia). FIG. 8 shows a table 802 that includes the calculation results based on the computer simulation. For purposes of illustration, the vector energy ratio Vector_Energy_area_Ratio$_{RP-RT}$ was determined. As can be observed, position P2 showed more signal distortions than positions P1 and P3, which means position P2 is determined as the highest priority cardiac site for electrical shock and ablation. For all positions along the catheter for ICD equipment 702, continuous monitoring of different positions (e.g., P1, P2, P3, etc.) greatly facilitates real-time diagnosis and treatment. Especially for P2, normal standard clinical methods (ST segment elevation voltage changes) is 0.01 mV for early ischemia event and 0.08 mV for late ischemia, which would not have crossed the standard 0.1 mV threshold to generate a warning. The ROI vector signal energy area ratio (Vector Energy area Ratio$_{RP-RT}$) showed more than 100% change in value for early ischemia and more than 200% change in value for late ischemia. This indicates that the signal portion vector ratio analysis may greatly help more sensitive and reliable detection of ventricular ischemia events. Different kinds of tests and probability analysis may further be used to find the specific type of cardiac arrhythmia.

In summary, multi-channel signal ROI vector analysis advantageously provides an efficient approach for cardiac function mapping, diagnosing severity-location-type of the pathology, predicting cardiac event trends, and providing suggestions for effective treatment and priority workflow. Additionally, multi-channel signal vector parameters, ratios and/or indices can be mapped to a two-dimensional or three-dimensional visual representation of the heart. Furthermore, multi-dimensional signal vector ratio information mapping may be used in real-time cardiac function diagnosis (signal vector ratio mode vs. time). By using multi-channel signal vector energy distribution information mapping, the abnormal tissue location, potential abnormal pathway, arrhythmia severity, etc., may be visually mapped and predicted, which provides informative feedback to the clinical user for providing additional treatment and drug delivery. The present techniques of cardiac signal energy mode estimation and patient healthy status characterization can be safely and easily implemented in pacemakers and cardiac implantable devices for characterizing and treating patient cardiac pathology and arrhythmia by using, for example, ICEG signals.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A computer-implemented method of patient signal analysis, comprising:
   receiving, from a patient monitor, a patient signal data waveform;
   generating, by a processor, a set of vectors directed from a common center on the patient signal data waveform to points of interest on the patient signal data waveform;
   extracting, by the processor, one or more vector parameters from the set of vectors; and
   determining, by the processor, one or more vector ratios based on the one or more vector parameters to monitor changes in the patient signal data waveform.

2. The method of claim 1 wherein the patient signal data waveform comprises an electrocardiogram waveform.

3. The method of claim 1 wherein generating the vectors comprises generating the vectors directed from an R wave peak center point on the patient signal data waveform.

4. The method of claim 1 wherein generating the vectors comprises generating the vectors directed from the common center point to at least one of P, Q, S, T or U wave peak points on the patient signal data waveform.

5. The method of claim 1 wherein generating the vectors comprises generating the vectors directed from the common center point to an H point defined at a half cycle time point.

6. The method of claim 1 wherein extracting the one or more vector parameters comprises extracting one or more time durations measured from a half cycle time stamp to time stamps of the points of interest.

7. The method of claim 6 wherein determining the one or more vector ratios comprises determining at least one ratio of distances associated with two vectors selected from the set of vectors.

8. The method of claim 6 wherein determining the one or more vector ratios comprises determining at least one ratio of time durations associated with two vectors selected from the set of vectors.

9. The method of claim 6 wherein determining the one or more vector ratios comprises determining at least one ratio comparing a vector amplitude associated with a first vector to a time duration associated with a second vector, wherein the first and second vectors are selected from the set of vectors.

10. The method of claim 9 wherein the first and second vectors are different.

11. The method of claim 9 wherein the first and second vectors are same.

12. The method of claim 1 wherein extracting the one or more vector parameters comprises extracting vector circles, wherein each of the vector circles is centered at the common center and has a radius defined by one of the vectors.

13. The method of claim 12 wherein determining the one or more vector ratios comprises determining at least one ratio of areas associated with two of the vector circles.

14. The method of claim 12 wherein determining the one or more vector ratios comprises determining at least one ratio that compares an area associated with a vector circle of first vector with a time duration associated with a second vector, wherein the first and second vectors are selected from the set of vectors.

15. The method of claim 1 wherein the one or more vector ratios are determined based on vector parameters extracted from the vectors within a single cycle of the patient signal data waveform.

16. The method of claim 1 wherein determining the one or more vector ratios comprises determining one or more unilateral ratios from the vectors.

17. The method of claim 1 wherein determining the one or more vector ratios comprises determining one or more bilateral ratios from the vectors.

18. The method of claim 1 further comprising determining one or more statistical indices based on the vector ratios.

19. The method of claim 1 further comprising mapping, via an artificial neural network, the one or more vector ratios and patient data to a cardiac event or pathology.

20. The method of claim 17 wherein mapping the one or more vector ratios and the patient data to the cardiac event or pathology comprises determining a location, type or severity of cardiac arrhythmia.

21. A non-transitory computer readable medium embodying a program of instructions executable by machine to perform steps for cardiac function characterization, the steps comprising:
- detecting an R wave peak of a patient signal data waveform;
- generating a set of vectors directed from the R wave peak to points of interest on the patient signal data waveform;
- extracting one or more vector parameters from the set of vectors; and
- determining one or more vector ratios based on the one or more vector parameters to monitor changes in the patient signal data waveform.

* * * * *